United States Patent [19]

Fukui et al.

[11] Patent Number: 4,772,114
[45] Date of Patent: Sep. 20, 1988

[54] DYNAMIC OPTOMETER

[75] Inventors: Yukio Fukui; Tsunehiro Takeda; Takeo Iida, all of Ibaraki, Japan

[73] Assignee: Agency of Industrial Science and Technology, Tokyo, Japan

[21] Appl. No.: 881,699

[22] Filed: Jul. 3, 1986

[30] Foreign Application Priority Data

Jul. 3, 1985 [JP] Japan .................................. 60-146227

[51] Int. Cl.[4] .............................................. A61B 3/10
[52] U.S. Cl. ..................................... 351/211; 351/221
[58] Field of Search ............... 351/210, 211, 220, 221, 351/237

[56] References Cited

U.S. PATENT DOCUMENTS 4,264,152  4/1981  Crane .
4,373,787  2/1983  Crane et al. ........................ 351/210

FOREIGN PATENT DOCUMENTS 61-52850  1/1986  Japan .

Primary Examiner—Rodney B. Bovernick
Assistant Examiner—Jay Ryan
Attorney, Agent, or Firm—Oblon, Fisher, Spivak, McClelland & Maier

[57] ABSTRACT

In a dynamic optometer, a variation in the direction of a subject's eye, namely, in the direction of gaze is measured by a direction detector to tilt a bi-axial rocking mirror according to the output of the detector, and an actual image of an eyeball formed by a pair of concave spherical mirrors is reflected to an optical system by the rocking mirror varying the direction of incidence. A second actual image which is formed immediately before a light source by the optical system is stably fixated in one direction, so that the eye is irradiated with light constantly from the front side in spite of eye movements. Accordingly, the refractive power can be measured, unaffected by the movement of an eyeball.

8 Claims, 2 Drawing Sheets

DYNAMIC OPTOMETER

BACKGROUND OF THE INVENTION

1. Field of the Invention

This invention relates to a dynamic optometer which is capable of measuring the refractive power of an eye from outside.

2. Description of the Prior Art

The conventional instruments for measuring the refractive power of eye are generally arranged to irradiate an eyeball with high-frequency pulses of infrared light which is converged into a beam, and a light spot which is formed on a retina as a secondary light source is imaged on a photo-detector to calculate the refractive power from the difference in position on the photodetector.

However, the instruments of this sort require the to project infrared light from the front side of an eyeball. For this purpose, the direction of gaze of a subject has to be fixed in a straight forward direction, which causes considerable strain to the subject.

In order to lessen the strain on the part of the subject, the present inventors proposed in a prior co-pending application (Japanese Laid-Open Patent Application No. 61-52850) a dynamic optometer arranged to permit eye movements during measurements. This dynamic optometer employs an elliptic mirror to shift the apparent eye position, and a mirror which is rockable about two perpendicularly intersecting axes according to eye movements to establish an apparently fixed eye.

FIG. 4 diagrammatically illustrates the outline of the above-mentioned dynamic optometer, in which indicated at 1 is a light source/receiver which projects an infrared beam and receives the reflected light from the fundus to measure the refractive power, at 2 a flat mirror which is rockable about two axes, at 3 and 4 elliptic mirrors, and at 5 a subject's eyeball.

In this instance, when the eyeball 5 is in the direction indicated by the solid line, the flat mirror 2 is held in the position similarly indicated by the solid line by detection of the eyeball direction. Accordingly, the beam is projected into the eyeball 5 from its front side in the direction of gaze as indicated by arrows of the solid line. If the eyeball is turned to the direction indicated by the broken line, the flat mirror 2 is tilted into the position indicated by the broken line, projecting the beam into the eyeball 5 straight from the front side through the light path of the broken line in spite of the eye movement.

Although the elliptic mirrors 3 and 4 have a function equivalent to that of a lens, they have different lens characteristics at different positions on the elliptic surface due to variations in radius of curvature. Consequently, it becomes necessary to make corrections for the projection of the beam and measurement of reflected light by means of a computing circuit which is provided in the instrument.

Besides, there is another problem that the use of elliptic mirrors of high accuracy which are relatively difficult to machine is reflected by a considerable increase in cost of the instrument as a whole.

SUMMARY OF THE INVENTION

It is an object of the present invention to provide an economical dynamic optometer which permits eye movement during measurement of the refractive power, employing inexpensive spherical concave mirrors in place of costly elliptic mirrors.

It is another object of the invention to provide a dynamic optometer which can dispense with a corrective computing means for the measurement of the refractive power.

A further object of the invention is to provide a dynamic optometer which can measure the refractive power unaffected by eye movements changing the direction of gaze, permitting to measure the refractive power of even a subject who is actually preforming desk work.

In accordance with the present invention, the foregoing objects are achieved by the provision of a dynamic optometer, which comprises: a light source for projecting an infrared beam into an eyeball; a direction detector for detecting changes in the direction of gaze; a pair of concave mirrors for focusing the actual image of the eyeball on a reflecting surface of a bi-axially rockable mirror: an optical system for focusing the actual image as a second actual image at a position optically equivalent to the eye position and opposing the light source; a mirror rocking mechanism for tilting the bi-axially rockable mirror according to the output of the direction detector for stabilizing the second actual image in spite of eye movements; and a refractometer for measuring the refractive power on the basis of a deviation of the position of reflected light from the fundus.

With the dynamic optometer of the above-described arrangement, a change in the direction of an eyeball, namely in the direction of gaze is detected by the direction detector, and the bi-axially rockable mirror is tilted according to the output of the direction detector in such a manner that the actual image of the eye formed by the paired concave mirrors is reflected into the optical system by the bi-axially rockable mirror changing the direction of incidence. A second actual image which is formed immediately before the light source by the optical system is stably fixed by the action of the mirror in spite of eye movements, constantly irradiating the eye ball from the front side during measurement of the refractive power irrespective of the direction of the eyeball.

The above and other objects, features and advantages of the invention will become apparent from the following description and the appended claims, taken in conjunction with the accompanying drawings which show by way of example a preferred embodiment of the invention.

DESCRIPTION OF PREFERRED EMBODIMENTS

Before going into detail description of the embodiment of the invention, the principles of measurement according to the invention are explained with reference to FIG. 2.

Figure 2:
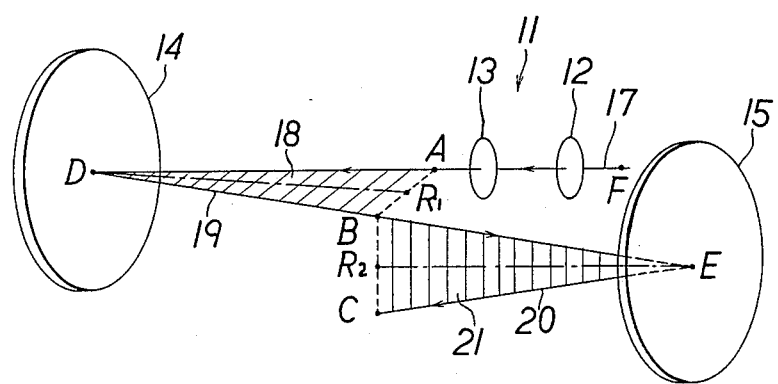
FIG. 2 is a diagrammatic view of a relay optical system employed by the optometer of FIG. 1.

FIG. 2 diagrammatically shows a relay optical system employed by the present invention, including a couple of lenses 12 and 13 of an optical system 11, located forward of a light source, and a couple of opposing concave mirrors 14 and 15 for receiving a light beam from the optical system. The respective optical elements are positioned such that a light beam 17 from the light source is projected into an eye at point C through light paths indicated by arrows.

Namely, the light beam 17 which is passed through the lenses 12 and 13 and through point A, which is slightly deviated from the center $R_1$ of curvature of the concave mirror 14 in a horizontal plane 18, is reflected at a center point D of the concave mirror 14 and converges to point B located in the plane 18 symmetrically with point A relative to the center $R_1$ of curvature. This point B is located vertically slightly above the center $R_2$ of curvature of the concave mirror 15, which is positioned such that the light beam passing straight through the point B is directed toward its center E. The light beam 20 which is reflected at the center E is directed toward point C located symmetrically with point B in a vertical plane 21 relative to the center $R_2$ of curvature of the concave mirror 15.

Accordingly, if the light source is located at point A, its actual image is formed at point B by the concave mirror 14, and then at point C by the concave mirror 15. Since the points A and B are deviated from the optical axis $\overline{DR_1}$ of the concave mirror 14 and similarly the points B and C are deviated from the optical axis $\overline{ER_2}$ of the concave mirror 15, "coma" aberrations occur to the images which are formed at points B and C. However, as these points are deviated in perpendicularly intersecting directions, the respective aberrations are offset to some extent when the image at point B is formed again at point C, reducing the aberrations as a whole.

As will be gathered from the foregoing description, when the light source is located at point A, its actual image is obtained at point C. On the contrary, if an eye is located at point C, its actual image is formed at point A.

Figure 3:
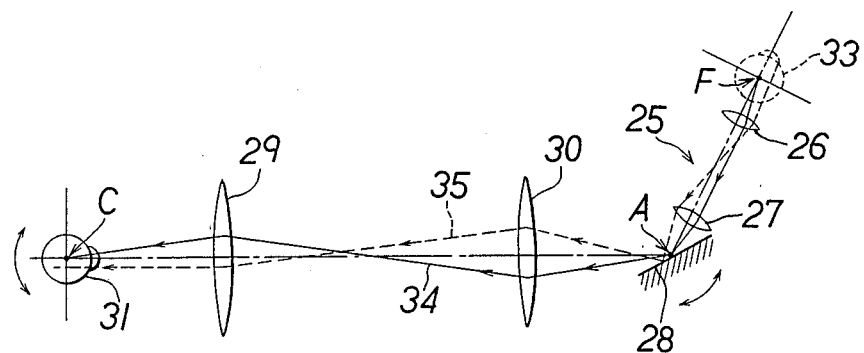
FIG. 3 is a diagrammatic view of an equivalent optical system.
Figure 4:
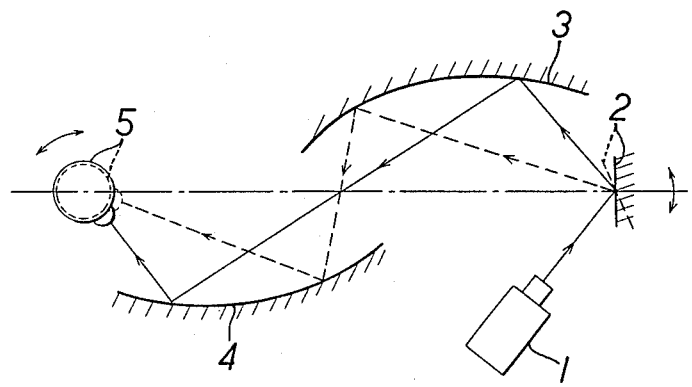
FIG. 4 is a diagrammatic view of a conventional optometer.

In the above-described optical relay system, the concave mirrors 14 and 15 are regarded as being equivalent to a convex lens. Illustrated in FIG. 3 is an equivalent optical system using a convex lens, in which denoted at 25 is an optical system constituted by lenses 26 and 27, at 28 a rocking mirror which is located at point A, at 29 and 30 convex lenses equivalent to the concave mirrors 14 and 15. A first actual image of an eye which is located at point C is formed at point A, and a second actual image 33 is formed at point F on the basis of the first actual image.

Namely, the light beam which is projected through point A is focused on point C through the equivalent convex lenses 30 and 29. The optical system 25 with lenses 26 and 27 constitutes a relay system as a whole, and gives an example of the lens system which avoids location of a lens at point A.

For instance, in case lenses 29 and 30 having a focal length f are used in combination with lenses 26 and 27 having a focal length f/2, setting the lenses 29, 30, 27 and 26 with intervals of 4f, 5f/2 and 3f/2, the optical relay system of FIG. 3 forms an optically equivalent system except that point F located f/2 outward of the lens 26 and point C located 2f outward of the lens 29 are inverted relative to the optical axis. Therefore, for instance, a beam 35 which is parallel with the optical axis at point F is in parallelism with the optical axis also at point C. Accordingly, if an eye 31 is located at point C, its actual image is formed at point A, and a second actual image 33 is formed at point F, shifting the apparent position of the eye 31 to point F.

In this instance, even if the eyeball 31 is rotated about point C by a small angle, its actual image 33 at point F can be fixed in one direction, without rotating, by turning the rocking mirror 28 about point A by half the angle of rotation of the eyeball, permitting to project the beam into the eye constantly from the front side thereof. Consequently, the refractive force can be measured by receiving the reflected light from the eye.

Figure 1:
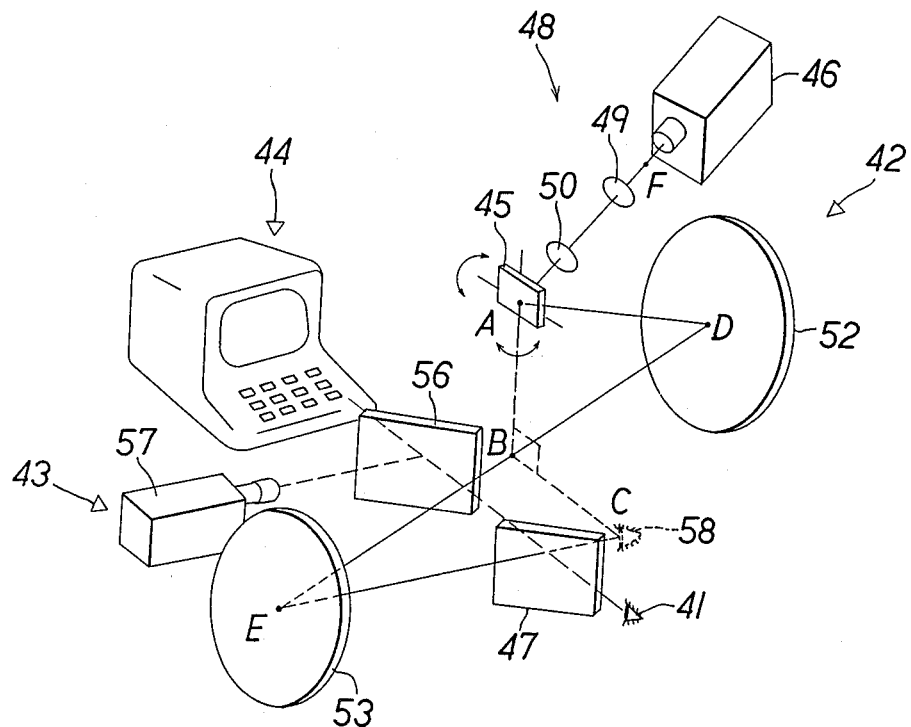
FIG. 1 is a diagrammatic view showing the general arrangement of a dynamic optometer embodying the invention.

Now, an embodiment 42 of the present invention, based on the above-described principles, is described with reference to FIG. 1, in which indicated at 41 is an eyeball of a subject, and which includes: a light source/refractometer 46 which projects infrared beam pulses into the eye 41 and measures its refractive power by receiving reflected light from the fundus; and a direction detector 43 which detects changes in the direction of gaze of the eye 41 from the position of reflection on the cornea of the projected infrared light. For the light source/refractometer 46 and direction detector 43, there may be employed conventional devices without making any change thereto. Indicated at 44 is a information I/O device which is used as a view target, and at 45 a bi-axial rocking mirror which is rotatable about two perpendicularly intersecting axes. If desired, a couple of mirrors which are respectively rotatable about one axis may be located in such a manner as to secure an optical effect equivalent to the bi-axial rocking mirror.

With this dynamic optometer, a change in the direction of gaze of the eye 41 is detected by the direction detector 43, and the bi-axial rocking mirror 45 is tilted according to the output of the direction detector, thereby permitting to project the infrared light into the eye 41 constantly from the front side during the measurement of the refractive power irrespective of movements of the eye 41.

Namely, the light source/refractometer 46 is arranged substantially in the same manner as the optical relay system of FIGS. 2 and 3, including a light source/receiver 46 for projecting a beam of infrared light modulated into pulses and measuring the refractive power by receiving reflected light from the fundus. Located between the light source/receiver 46 and the dichroic mirror 47 forward of the eye 41 are: an optical system 48 having a couple of lenses 49 and 50 similar to the ones as described hereinbefore in connection with FIGS. 2 and 3; a bi-axial rocking mirror 45; and a pair of opposing spherical concave mirrors 52 and 53. The mirror 47 which is located forward of the eye 41 reflects infrared light while permitting passage of visible light. Therefore, by the above-described action of the optical relay system, the infrared light from the light source/receiver 46 irradiates the eye 41. This means that an actual image of the eye 41 is formed at point F.

As mentioned hereinbefore, by tilting the bi-axial rocking mirror 45 about both or one of the two axes through a certain angle, the actual image which is formed by the optical relay system can be fixated irrespective of eye movements to irradiate the eye 41 with the infrared light constantly from the front side.

The tilting angle of the bi-axial rocking mirror 45 is determined according to the output of the direction detector 43, which detector 43 is provided with a photodetector like a TV camera 57 which is directed toward reflected light from a half-mirror 56 located between a mirror 47 and the information I/O device 44. Thus, the image of the eye 41 is cast to the photodetector 57 through the mirror 47 and half-mirror 56 to detect the direction of gaze of the eye 41, sending drive signals according to the output of the photodetector to a mirror drive mechanism (not shown) to tilt the rocking mirror 45 accordingly. The picture image of the information I/O device 44 as a view target reaches the eye 41 through the half-mirror 56 and mirror 47. Since the subject can see the picture image on the information I/O device through these mirrors, he or she can receive a measurement in a natural way.

In the above-described dynamic optometer, an actual image of the eye 41 is formed at point A on the reflecting surface of the rocking mirror 45 by the mirror 47 and paired concave mirrors 53 and 52. This actual image is reflected toward the optical system 48 by the rocking mirror 45, forming a second actual image at point F. Therefore, the second actual image at point F can be fixated relative to the refractometer 46 by varying the direction of incidence of the actual image of the eye 41 on the optical system 48 by tilting the rocking mirror 45 correspondingly to the eye movements.

Namely, the direction of the eye 41 is always detected by the direction detector 43, and a drive signal corresponding to this detected value is fed to the mirror drive mechanism, and thereby the mirror 45 is tilted in a direction or directions following an eye movement to project the infrared beam pulses from the light source/receiver on the eye 41 constantly from the front side thereof.

In this manner, the light source/receiver 46 measures the refractive power of the eye 41 on the basis of a positional deviation of incoming reflected light of the eye 41 which is irradiated with the infrared light from the front side.

A mirror image 58 of the eye 41 is formed at point C by the mirror 47. From a standpoint of reducing aberrations, it is desirable that the angle ABC is approximately right angles.

What is claimed is:

1. A dynamic optometer, which comprises:
   (a) a light source for irradiating a subject's eyeball with beam-like infrared light;
   (b) a direction detector for detecting the direction of gaze of the eyeball;
   (c) a bi-axial rocking mirror;
   (d) a pair of opposingly located spherical concave mirrors, said concave mirrors being arranged with respect to said rocking mirror such that the beam-like light which passes through a point slightly deviated from the center of curvature of one of said concave mirrors and is then reflected at the center of said mirror, is thereafter passed through a point slightly deviated both from the center of curvature of said spherical concave mirror and from the center of curvature of said other mirror and then is directed toward the center of said other mirror, and an actual image of the eyeball is formed on a relecting surface of said bi-axial rocking mirror;
   (e) optical system means for forming a second actual image at a position opposing said light source and optically equivalent to the eye position;
   (f) a mirror rocking mechanism for tilting said bi-axial rocking mirror according to an output of said direction detector thereby to fix said second actual image irrespective of eye movement; and
   (g) a refractometer for measuring the refractive power of the eyeball on the basis of positional deviation of reflected light from the fundus of the eyeball.

2. The dynamic optometer defined in claim 1, wherein said bi-axial rocking mirror is constituted by a single mirror rockable about two perpendicularly intersecting axes.

3. The dynamic optometer defined in claim 1, wherein said light source and refractometer are integrated into a light source/receiver capable of irradiating said eye with an infrared beam modulated into pulses and measuring the refractive power of said eye on the basis of reflected light from the fundus.

4. The dynamic optometer defined in claim 3, further comprising, between said light source/receiver and a mirror located in front of said eye, an optical system having two lenses, said bi-axial rocking mirror and two opposingly located concave mirrors.

5. The dynamic optometer defined in claim 3, wherein said mirror located in front of said eye reflects infrared light while passing visible light, projecting said infrared light on said eye by reflection of said mirror and permitting a subject to see a view target through said mirror.

6. The dynamic optometer as claimed in claim 1, wherein the two planes of incidence of the beam-like light on said spherical mirrors are perpendicular to each other.

7. The dynamic optometer as claimed in claim 1, wherein said direction detector comprises means for detecting a change of direction of the eyeball by detecting a reflecting light at a cornea of said eyeball with a light receiving member.

8. The dynamic optometer of claim 7 wherein said light receiving member is a TV camera.

* * * * *